(12) United States Patent
Stroebech et al.

(10) Patent No.: US 7,862,878 B2
(45) Date of Patent: Jan. 4, 2011

(54) LAYERED ADHESIVE CONSTRUCTION USEFUL FOR ATTACHING A COLLECTING BAG OR COLLECTING DEVICE TO THE PERIANAL AREA

(75) Inventors: Esben Stroebech, Hoersholm (DK); Anders Bach, Copenhagen S (DK); Claus Bo Voge Christensen, Snekkersten (DK); Danuta Ciok, Nivaa (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 12/227,643

(22) PCT Filed: May 23, 2007

(86) PCT No.: PCT/DK2007/050059
§ 371 (c)(1),
(2), (4) Date: Nov. 24, 2008

(87) PCT Pub. No.: WO2007/134612
PCT Pub. Date: Nov. 29, 2007

(65) Prior Publication Data
US 2009/0148661 A1 Jun. 11, 2009

(30) Foreign Application Priority Data
May 24, 2006 (DK) ................. 2006 00711

(51) Int. Cl.
*B32B 3/24* (2006.01)
*A61F 5/44* (2006.01)
*A61F 5/443* (2006.01)

(52) U.S. Cl. ............... 428/137; 428/66.6; 428/68; 428/131; 428/156; 428/189; 428/195.1; 428/343; 604/317; 604/327; 604/332; 604/336; 604/337; 604/338

(58) Field of Classification Search ............. None
See application file for complete search history.

(56) References Cited

U.S. PATENT DOCUMENTS 3,712,304 A * 1/1973 Marsan ............. 604/336
3,713,445 A * 1/1973 Marsan ............. 604/336
3,734,096 A * 5/1973 Millenbach ........... 604/355

(Continued)

FOREIGN PATENT DOCUMENTS

DE 2813708 A1 * 10/1978

(Continued)

*Primary Examiner*—Patricia L Nordmeyer
*Assistant Examiner*—Jeff A Vonch
(74) *Attorney, Agent, or Firm*—Jacobson Holman PLLC

(57) ABSTRACT

A layered adhesive construction including a layer of a moldable paste wrapped in one or more wrapping layers, and a first adhesive layer attached to the wrapping layer on one outer surface of the layer of wrapped moldable paste where the layered adhesive construction has a symmetrical shape around a central axis of symmetry lying in the plane of the layers of the adhesive construction. The adhesive construction has a hole going therethrough which is placed with its center on the axis of symmetry so that it divides the central axis of symmetry in two parts. An area around at least one of the two parts on the central axis of symmetry is without the moldable paste layer and has one or more backing layers and a layer of adhesive on the same side of the adhesive construction as the first adhesive layer.

19 Claims, 2 Drawing Sheets

U.S. PATENT DOCUMENTS

Figure 1:
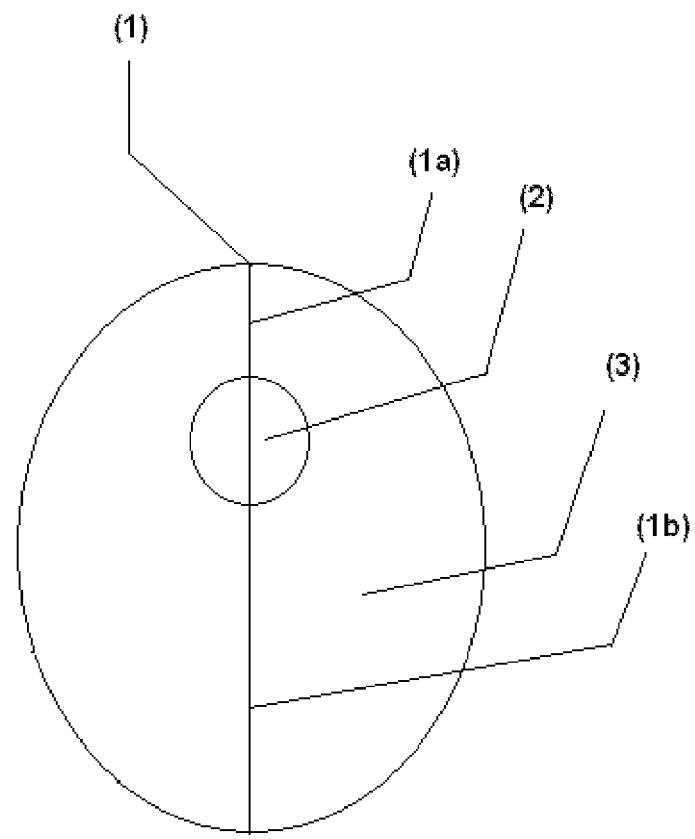

| | | | | |
|---|---|---|---|---|
| 3,805,789 | A * | 4/1974 | Marsan | 604/336 |
| 3,898,990 | A * | 8/1975 | Nolan | 604/336 |
| 4,222,923 | A * | 9/1980 | Rhodes et al. | 524/169 |
| 4,252,120 | A * | 2/1981 | Carpenter | 604/336 |
| 4,403,991 | A * | 9/1983 | Hill | 604/337 |
| 4,445,898 | A * | 5/1984 | Jensen | 604/337 |
| 4,475,908 | A * | 10/1984 | Lloyd | 604/339 |
| 4,867,748 | A * | 9/1989 | Samuelsen | 604/336 |
| 4,917,692 | A * | 4/1990 | Steer et al. | 604/355 |
| 5,015,244 | A * | 5/1991 | Cross | 604/344 |
| 5,051,259 | A * | 9/1991 | Olsen et al. | 424/443 |
| 5,496,296 | A * | 3/1996 | Holmberg | 604/336 |
| 5,545,154 | A * | 8/1996 | Oberholtzer | 604/336 |
| 5,591,447 | A * | 1/1997 | Jensen | 424/443 |
| 5,593,397 | A * | 1/1997 | La Gro | 604/355 |
| 6,451,883 | B1 | 9/2002 | Chen et al. | |
| 6,764,474 | B2 * | 7/2004 | Nielsen et al. | 604/344 |
| 6,814,720 | B2 * | 11/2004 | Olsen et al. | 604/339 |
| 7,101,357 | B2 * | 9/2006 | Tanaka et al. | 604/338 |
| 2003/0004477 | A1 * | 1/2003 | Nielsen et al. | 604/336 |
| 2003/0088219 | A1 * | 5/2003 | Metz et al. | 604/339 |
| 2003/0150050 | A1 * | 8/2003 | Tanaka et al. | 4/144.3 |
| 2004/0127839 | A1 * | 7/2004 | Sigurjonsson et al. | 602/55 |
| 2005/0096611 | A1 * | 5/2005 | Stoyer et al. | 604/332 |

FOREIGN PATENT DOCUMENTS

| | | |
|---|---|---|
| EP | 0 686 381 A1 | 12/1995 |
| EP | 1 527 789 A1 | 5/2005 |
| WO | WO 98/17212 | 4/1998 |
| WO | WO 98/17329 | 4/1998 |
| WO | WO 2004062536 A1 * | 7/2004 |
| WO | WO 2007/076862 A1 | 7/2007 |

* cited by examiner

LAYERED ADHESIVE CONSTRUCTION USEFUL FOR ATTACHING A COLLECTING BAG OR COLLECTING DEVICE TO THE PERIANAL AREA

This is a national stage of PCT/DK07/050,059 filed May 23, 2007 and published in English, which has a priority of Denmark no. PA 2006 00711 filed May 24, 2006, hereby incorporated by reference.

FIELD OF THE INVENTION

The present invention relates to a layered adhesive construction particularly useful for attaching a collecting bag or collecting device to the perianal skin or other areas of the skin with a folded or irregular surface, which is subjected to moisture and/or aggressive fluids. The layered adhesive construction comprises a layer of a mouldable paste wrapped in one or more wrapping layers and a layer of adhesive on the skin contacting surface.

BACKGROUND OF THE INVENTION

In the intensive care units of hospitals (ICU), the patients often have thin water-like stools, which may be very aggressive to the perianal skin. For management of stools, diapers, faecal collecting bags or anal invasive products are used. The diapers often result in damaged skin and require frequent change and the invasive products are expensive. Collecting bags attached to the perianal skin is an attractive solution, but the devices on the market today have problems with a high degree of leakage.

U.S. Pat. No. 4,445,898 having Hollister Inc. as assignee describe a faecal incontinence device where an adhesive ring formed construction is used to attach a collecting device to the perianal area.

The company Hollister Inc. have products on the market, which consist of a collecting device with an adhesive construction designed for adhering to the perianal skin. One of the products comprises a 2 mm paste like adhesive with a foam-like backing welded to an open bag. The adhesive construction is circular (Φ110 mm) and has a 35 mm hole placed at a distance for the center of the adhesive construction. Before use a strip of release liner is removed from the adhesive surface and the adhesive construction is bend so that adhesive surface may be placed between the buttocks and on the perianal skin. Another product comprises a more elastic adhesive on a non-woven backing.

It has been found that by using a layered adhesive construction with a mouldable paste, e.g. a mouldable hydrocolloid adhesive, wrapped in one or more wrapping layers and having a skin friendly adhesive on the skin contact surface, provides a good leak resistant construction which may be shaped to fit folded or irregular skin surfaces. The adhesive construction of the invention is particularly useful for attaching collecting bags or collecting devices to the perianal area or around an ostomy.

Adhesive constructions comprising layers of hydrocolloid adhesives are well known in the art:

EP 1 527 789 A1 describes a construction comprising a film layer and at least two layers of hydrocolloid adhesives with different composition.

The prime object of the adhesive construction described therein is to provide a multi-layered adhesive medical appliance that has the attributes of a skin friendly wet tack pressure sensitive adhesive for use adjacent to the skin, and a flexible, comfortable, moisture tolerant adhesive that resists degradation after sterilization, and is capable of creating a seal around the stoma in a controlled fashion, for use away from the skin.

It is described that a disadvantage of the known skin-friendly adhesives used adjacent to the skin is that they tend to be somewhat rigid when they become too thick. Thus according to this application, it is preferred that the adhesive layer adjacent to the skin is thinner than the more flexible, comfortable, moisture tolerant adhesive, which is used away from the skin.

EP 1 527 789 A1 also describes that one of the adhesive layers may be of a mouldable hydrocolloid adhesive, and the mouldable adhesive layer in the construction is the one of the two adhesive layers placed between the skin contact adhesive and the film backing.

The adhesive construction according to the invention differ from the adhesive construction in EP 1 527 789 in that the mouldable paste is completely enveloped or enclosed in one or more wrapping layers, thereby preventing the mouldable paste from flowing out on the skin and leaving residues of the mouldable paste on the skin of patients.

EP 686 381 describes similar adhesive constructions with two layers of hydrocolloid adhesives with different composition. According to this patent application, the layer of adhesive securing the adhesive construction to the skin is composed of a skin friendly hydrocolloid containing adhesive that has a relatively low resistance to dissolution and/or disintegration when contacted by stomal fluids, whereas the other adhesive layer placed away from the skin is composed of a relatively soft, easy-deformable and extrudable adhesive sealant material that is more resistant to dissolution or disintegration by stomal fluids than the material of the skin contact adhesive. From the drawings it is clear that the adhesive layer adjacent to the skin is thinner than the adhesive layer placed away from the skin.

The adhesive construction according to the invention differ from the adhesive construction according to EP 686 381 in that the mouldable paste is completely wrapped in one or more wrapping layers, thereby preventing the mouldable mass from flowing out on the skin and leaving residues of the mouldable paste on the skin of patients.

WO 98/17212 relates to a separate sealing member for use in connection with ostomy appliances. The separate sealing member may be in the form of a mouldable ring or paste of a hypo-allergenic adhesive, which during use is placed in the hole of the wafer of an ostomy appliance to seal around the stoma. FIGS. 7 and 8 relates to a particular embodiment where the sealing member is in the form of a mouldable ring with a core of soft, easy deformable, non-memory putty like material wrapped in a thin, flexible wrapping material. The wrapping material may be a water permeable membrane coated with a skin friendly adhesive on the outside or the wrapping material may itself be a skin friendly hydrocolloid-containing barrier adhesive.

It is described that the wrapping material improves the performance of the mouldable ring due to the elimination of the risk of dissolution of the deformable core material and the elimination of the risk that residues of the core material is left on the skin after removal of the sealing member.

It has now been found that a layered adhesive construction comprising a layer of a mouldable paste wrapped in one or more wrapping layers, and comprising a first adhesive layer attached to the wrapping layer on one outer surface of said layer of mouldable paste wrapped in wrapping layer(s) is particularly useful for attaching collecting bags or collecting devices to the perianal skin.

The adhesive construction according to the invention differs from the adhesive construction described in WO 98/17212 in that the construction only has an adhesive on one of its outer surfaces and in that it has areas where the mouldable paste is absent. Furthermore, the adhesive construction of the invention preferably has a hole going through the construction, which hole is not place in the center of the construction but in one end of the construction. This position of the hole is an advantage when the adhesive construction is used to attach a collecting bag or collecting device to the perianal area, where the distance from the anus to the vagina respectively the scrotum, sets some limits with regard to the perianal area available for attaching the device.

SUMMARY OF THE INVENTION

The present invention thus relates to a layered adhesive construction comprising a layer of a mouldable paste wrapped in one or more wrapping layer(s), and comprising a first adhesive layer attached to the wrapping layer on one outer surface of said layer of wrapped mouldable paste wherein the layered adhesive construction has a symmetrical shape around a central axis of symmetry lying in the plane of the layers of the adhesive construction, and has a hole going through the adhesive construction, which hole is placed with its center on said axis of symmetry so that it divides the central axis of symmetry in two parts and wherein the adhesive construction comprises an area around at least one of said two parts of the central axis of symmetry, where the layered adhesive construction consist of one or more backing layers and at least one layer of adhesive attached to the backing layer(s) on the same side of the adhesive construction as the first adhesive layer. In this area around said part(s) of the central axis of symmetry, the wrapped mouldable paste is absent and it is possible to cut this part of the adhesive construction to fit the individual patient, while the mouldable paste is kept encapsulated between the wrapping layers.

In a preferred embodiment of the invention, the hole divides the central axis of symmetry in a short part and a long part.

According to a particularly preferred embodiment, the invention relates to a layered adhesive construction wherein the adhesive construction comprises (i) an area around the short part of the central axis of symmetry, or (ii) an area around both the short part and the long part of the central axis of symmetry, where the layered adhesive construction consist of one or more backing layers and at least one layer of adhesive on the same side of the adhesive construction as the first adhesive layer.

The invention also relates to a collecting device comprising a layered adhesive construction as above.

DETAILED DESCRIPTION OF THE INVENTION

As used herein a mouldable paste means a soft, easy deformable paste, which may be formed to the shape of a folded or irregular surface e.g. by finger pressure. Such pastes are well known in the art, see for example WO publication No. 98/17212.

As used herein mouldable wrapping layer means a wrapping layer, which may easy be deformed and formed e.g. by finger pressure to the shape of a folded or irregular surface.

As used herein a layer of mouldable paste wrapped in one or more wrapping layers means a mouldable paste sandwiched and completely enclosed between one or more wrapping layers.

The adhesive construction of the invention has a central axis of symmetry lying in the plane of the layers, and a hole going through the adhesive construction having its center placed on the central axis of symmetry. The hole divides the central axis of symmetry in two parts. In one embodiment, the hole divides the central axis of symmetry in a short part and a long part. The length of both the short part and the long part of the central axis of symmetry is defined by the distance between the peripheral edge of the adhesive construction and the nearest edge of the hole on said central axis of symmetry. The length of the short part is shorter than the long part.

The hole in said adhesive construction is preferably essentially circular.

The wrapping layers may be made of different materials. In one embodiment the wrapping layer is a layer sprayed on the layer of mouldable paste. In another embodiment the wrapping layers are welded together around the peripheral edges and around the hole in the layer of mouldable paste and optionally around the area(s) around said part(s) of the central axis of symmetry.

According to one embodiment of the invention, the layer of mouldable paste is wrapped between two wrapping layers, which are identical. Alternatively, the layer of mouldable paste is wrapped between two wrapping layer(s), which are different in chemical composition, physical structure and/or thickness.

Suitably the wrapping layer(s) wrapped around the layer of mouldable paste is selected from mouldable wrapping layers.

The wrapping layers enclosing the layer of mouldable paste prevents the mouldable paste from flowing out on the skin and eliminates the risk of leaving residues of the mouldable paste on the skin.

To be able to absorb moisture, the mouldable paste suitably comprises hydrocolloids or other absorbent materials and in this case it is important that the wrapping layers enclosing the mouldable mass allows moisture to pass into the mouldable paste. The wrapping layers also makes the mouldable paste less sensitive to disintegration following absorption of moisture as the wrapping layers prevent the moldable paste from falling apart.

The wrapping layer(s) may suitably be a liquid impermeable but moisture vapour permeable film, or it may be a film with perforations, a woven or a non-woven material.

The backing layer(s) carrying the adhesive layer in the above mentioned area(s) around said part(s) of the central axis of symmetry is suitably identical to one or more of the wrapping layers which is used as a wrapping material for the mouldable paste.

The backing layer(s) carrying the adhesive layer in the above mentioned area(s) around said part(s) of the central axis of symmetry may also be different from the wrapping layers which is used as a wrapping material for the mouldable paste. In this case the backing layer(s) is glued, welded or otherwise secured the wrapping layer(s) wrapped around the layer of mouldable paste.

The first adhesive layer is suitably a skin friendly adhesive providing high wet tack. Such adhesives may become too stiff if the layer is too thick. On the other hand the first adhesive layer may loose cohesion if it becomes too thin. The thickness of the first adhesive layer is typically between 0.3 and 0.7 mm, preferably around 0.5 mm.

The layer mouldable paste should have a certain thickness to be flexible and effective in relation to filling in irregularities in the surface to which the adhesive construction is attached.

The mouldable paste preferably comprises hydrocolloids capable of absorbing moisture from the first adhesive layer and the skin and the absorption capacity of the layer depends on the thickness of the layer of mouldable paste.

Thus, in one embodiment of the invention the thickness of the first adhesive layer is smaller than the thickness of the layer of mouldable paste.

The layer of mouldable paste is typically more than double as thick as the first adhesive layer. In a preferred embodiment the thickness of the first adhesive layer is ⅓ or below ⅓ of the thickness of the layer of the mouldable paste where the layers are thickest.

The thickness of the layer of the mouldable paste is suitably between 1-2.5 mm, preferably between 1.25-2.25 mm, more preferred 1.25-1.75 mm and most preferred about 1.5 mm.

According to a preferred embodiment the thickness of the first adhesive layer is 0.5 mm and the thickness of the layer of mouldable paste is 1.5 mm.

Suitably, both the first adhesive layer and the layer of the mouldable paste have a uniform thickness, except for optional beveled edges, such as the peripheral edges, the edge around the hole and the edges around the above mentioned area(s) around said part(s) of the central axis of symmetry.

The anatomy of the perianal area in humans is very diverse. One of the major differences exists between men and women, but the difference between individuals of the same sex is also considerable. Women have a short distance (1.7-3 cm) between the anus and the vagina and the distance from the scrotum to the anus in men is between 3-7 cm.

According to a particularly preferred embodiment, the invention relates to a layered adhesive construction wherein the adhesive construction comprises an area(s) around said parts of the central axis of symmetry, where the layered adhesive construction consist of one or more backing layers and at least one layer of adhesive on the same side of the adhesive construction as the first adhesive layer.

A particular advantage of this embodiment of the invention is that in this area around said parts of the central axis of symmetry the mouldable paste is absent and it is possible to cut this part of the adhesive construction to fit the anatomy of the individual patient, without the risk of the mouldable paste flowing out on the skin of the patients leaving residues which are difficult to remove.

According to a preferred embodiment, the adhesive construction of the invention comprises an area (i) around the short part or (ii) around the short part and the long part of the central axis of symmetry, where the layered adhesive construction consist of one or more backing layers and at least one layer of adhesive on the same side of the adhesive construction as the first adhesive layer.

The adhesive construction of the invention may in principle comprise further areas where the adhesive construction consists of one or more backing layer and an adhesive layer and where the mouldable paste is absent.

In one embodiment of the invention the adhesive carried on the backing layer(s) in said area around said part(s) of the central axis of symmetry is the same adhesive as in the first adhesive layer.

According to another embodiment, adhesive carried on the backing layer(s) in said area around said part(s) of the central axis of symmetry is different from the adhesive in the first adhesive layer.

According to still another embodiment of the invention the area around said part(s) of the central axis of symmetry consist of one or more backing layers and two layers of adhesives on top of each other, where an adhesive layer corresponding to the first adhesive layer is situated between said one or more backing layers and a second adhesive layer.

Suitably, the adhesive layer on the backing layer(s) in the above mentioned area around said part(s) of the central axis of symmetry is made of an adhesive providing stronger adhesion to skin than the first adhesive layer.

The area around said part(s) of the central axis of symmetry suitably corresponds to an area extending 0.25-3 cm to each side of said part(s) of the central axis of symmetry.

The above mentioned area around said part(s) of the central axis of symmetry extends from the outer peripheral edge of the adhesive construct to the edge of the hole.

Figure 2:
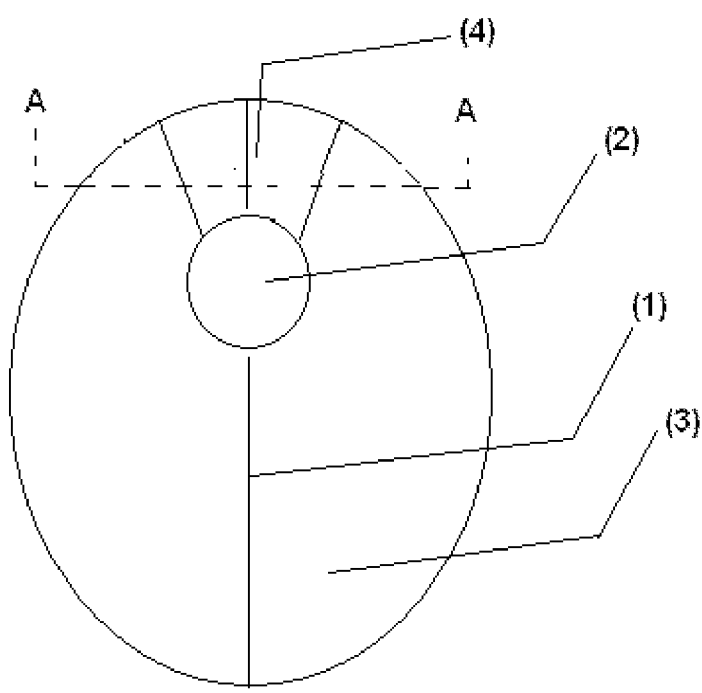
Figure 3:
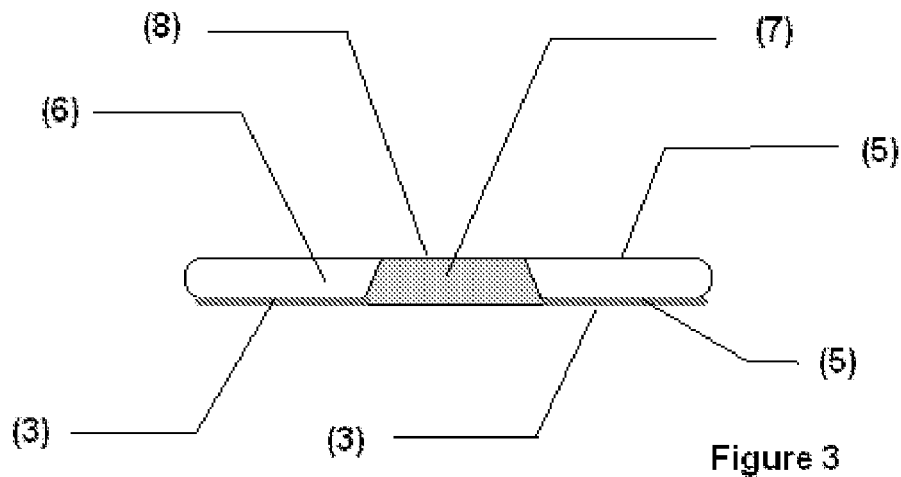

FIGS. 2-3 illustrates this preferred embodiment of the invention. The above mentioned area around the short part of the central axis of symmetry may have the contour illustrated in FIG. 2 or any other suitable shape. The adhesive construction of the invention may have a similar area around the long part of the central axis of symmetry.

According to one embodiment of the invention, the mouldable paste is a mouldable paste comprising hydrocolloids, such as a mouldable hydrocolloid adhesive. The layer of mouldable hydrocolloid adhesive wrapped in wrapping layers provides the adhesive construction with its ability to conform to irregular or folded surfaces, and provides a high moisture absorption capacity and erosion resistance.

The mouldable mass of the adhesive construction of the invention may be a mouldable hydrocolloid adhesive paste such as the ones described in WO 98/017329 and WO 98/17212.

The general composition of a mouldable hydrocolloid adhesive is:

1 to 20% by weight of a styrene block copolymer, 5 to 60% by weight of a tackifying liquid constituent in the form of a viscous polymeric material which is compatible with the block copolymer, 1 to 10% by weight of a constituent which is like wax in nature or appearance, and one or more hydrocolloids.

The adhesive composition used for the first adhesive layer is selected from adhesives having good initial wet tack, long wear time, good moisture absorption and good gel strength (ability to be removed in one piece).

The first adhesive layer is suitably a hydrocolloid adhesive such as the ones described in U.S. Pat. No. 6,451,883.

A general composition for the first adhesive layer could be: 5-20% of one or more styrene block copolymers 35-50% of one or more polybutenes, and 20-60% of one or more hydrocolloids.

An alternative composition could be: 20-40% polyisobutylene, 10-20% butyl rubber, 5-15% tackifier and 20-60% w/w of one or more hydrocolloids.

The adhesive layer on the backing layer(s) in the above mentioned area around said parts of the central axis of symmetry may also be of an adhesive which is different from the adhesive in the first adhesive layer, e.g. a silicone adhesive or another hydrocolloid adhesive, or a layer comprising two layers of different adhesives on top of each other.

Suitably, the layered adhesive construction of the invention has a circular, ellipsoid, oval or egg-formed contour when viewed from an angle perpendicular to the plane of the layers.

A contour for the adhesive construction of the invention is suitably an oval geometry of 90×80 mm with a 35 mm hole placed 25 mm (the center of the hole placed 42.5 mm) from the peripheral edge of the adhesive construction and on the longest axis of symmetry.

The edges of the adhesive construction of the invention may be beveled, both around the outer periphery, around the hole and around the area around said part(s) of the central axis of symmetry.

In the beveled portion, the mouldable layer may become thinner and may even disappear completely at some distance from the peripheral edge or the edge around the hole in the construction.

The adhesive construction of the invention is optionally covered, in part or fully, by one or more release liners, or cover films to be removed before or during application. A protective cover or release liner may for instance be siliconized paper. It does not need to have the same contour as the construction.

The protective cover is not present during the use of the construction of the invention and is therefore not an essential part of the invention. Furthermore, the construction of the invention may comprise one or more "non touch" grip (s) known per se for applying the dressing to the skin without touching the adhesive layer. Such a non-touch grip is not present after application of the construction. For larger constructions it is suitable to have two or three or even four "non-touch" grips.

The invention is illustrated more in detail in FIGS. 1-4.

FIG. 1 shows an adhesive construction of the invention seen from an angle perpendicular the layers of the construction. The adhesive construction have an oval shape with a central axis of symmetry (1) a hole (2) placed with its centre on the central axis of symmetry and dividing the central axis of symmetry in two parts; a short part (1a) and a long part (1b). The surface of the adhesive construction is covered with a first adhesive layer (3).

FIG. 2 shows an adhesive construction of the invention seen from an angle perpendicular the layers of the construction. The adhesive construction have an oval shape with a central axis of symmetry (1) a hole (2) placed with its centre on the central axis of symmetry and said hole dividing the central axis of symmetry in two parts where one part is shorter than the other. The surface of the adhesive construction is covered with a first adhesive layer (3) and in an area (4) around the short part of the central axis of symmetry, the adhesive construction consists of backing layer(s) and an adhesive layer. The invention covers both the embodiment where the adhesive in the adhesive layer (3) and the adhesive layer in the area (4) is identical in composition and different in composition. The adhesive layer in the area (4) may be of an adhesive that adheres stronger to the perianal skin of humans than the first adhesive layer (3). In use the adhesive in the area (4) is used to adhere the adhesive construction to the skin area between the anus and the scrotum or the vagina depending on the sex of the patient. The adhesive layer with backing in the area (4) may be cut and shaped to fit the individual patient.

FIG. 3 shows the cross-section marked A-A in FIG. 2. The mouldable mass (6) enveloped in a wrapping layer (5) carries on one side an adhesive layer (3) and in an area around the central axis of symmetry, the enveloped mouldable paste and the first adhesive layer is replaced with an adhesive layer (7). As mentioned above the adhesive in layer (3) and layer (7) may be of the same or of a different composition. The second adhesive layer may carry a backing (8), which may consist of the wrapping layer (5) as a single or as a double layer, or some other backing secured to the wrapping layer (5).

Figure 4:
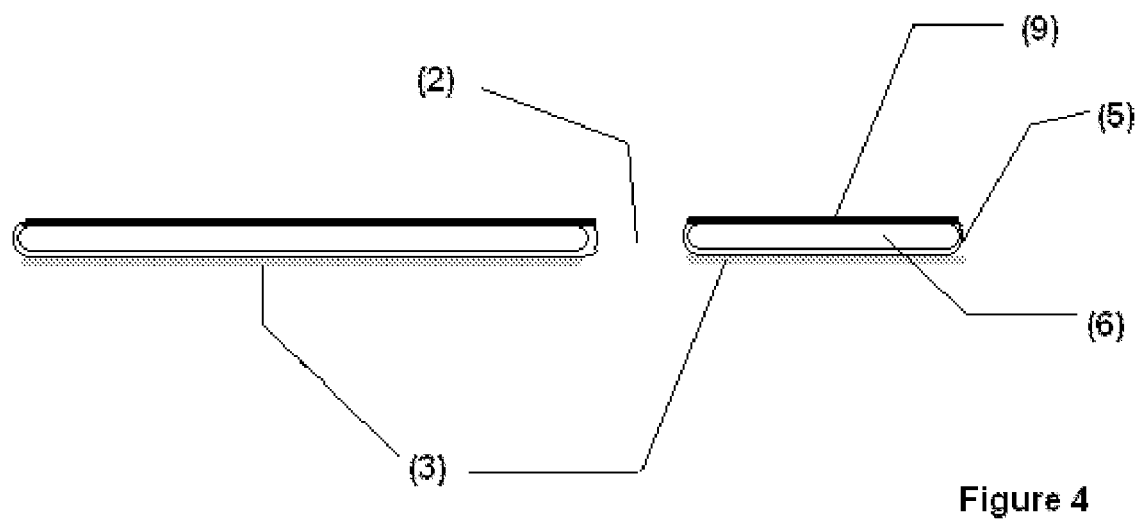

FIG. 4 show the layered construction of the invention with the mouldable paste (6) enveloped between a wrapping layer (5) and a wrapping layer (9) made of a different material. The backing layer (9) may be a layer useful for welding the adhesive construction to a collecting bag or a collecting device. The wrapping layers (5) and (9) may be welded together along the peripheral edge of the construction (welding not shown).

Some of the dimensions in the drawings have been exaggerated in order to illustrate the invention more clearly. The description contains a description of more realistic dimensions for the layers in the adhesive construction of the invention.

EXAMPLE

An adhesive construction according to the present invention is tested in a comparative test on 12 persons against a commercial available fecal management adhesive bag. The set up of the test and product description is described below Adhesives used in the test:

A dual layer adhesive construction according to the invention based on a 500 my adhesive bonding to the skin and a 1500 my paste incorporated between the skin adhesive and a top foil. The foil is welded to a bag. The skin adhesive is a standard semi plastic PSA sold under the brand name Assura, Easy Removal by Coloplast A/S and the paste is a slightly modified Strip paste, Coloplast A/S as described in PCT/DK2006/000722.

The competitive adhesive is the commercial available fecal collecting bag from Hollister with item nr. 9821.

The test set up is as follows:

A clinical test in the perianal area conducted by an independent company (Phase 1 Trails, Hvidovre, Denmark)

| | |
|---|---|
| Objects included: | 12 healthy volunteers (6 male and 6 female) |
| Wear time | 2 hours inspection and then 10 hours in bed (12 hours of wear time) |
| Preparation | Trimming in the peri anal area |
| Application | Applicated in the peri anal area by a Stoma Care Nurse |
| Evaluation | Evaluated by the Stoma Care Nurse |
| Output | No fecal output from the objects come into the bag, but 100 ml water is put into the bags in order to stress the adhesive and have a clear indication on leakage |
| Primary parameter | Leakage of water between the adhesive and the peri anal skin |
| Secondary parameter | Adhesive residues on skin and pain on removal. |

The result of the test was a lowering of the overall frequency of leakage from 63% leakage (2 hours and 12 hours leakage) compared to 25% leakage on the adhesive according to the invention. Adhesive residues were higher for the competitive product and pain was approximately the same.

The invention claimed is:

1. A layered adhesive construction for attaching to the perianal area of a patient comprising:
   a layer of a moldable paste wrapped in at least one wrapping layer;
   a first adhesive layer attached to the wrapping layer on one outer surface of said layer of wrapped moldable paste;
   said layered adhesive construction having a symmetrical shape around a central axis of symmetry lying in the plane of the layers of the adhesive construction, and having a hole going therethrough that is placed with its center on said axis of symmetry so that said hole divides the central axis of symmetry in two parts, and said adhesive construction including an area around at least one of said two parts on the central axis of symmetry where the layered adhesive construction is without the moldable paste layer and has of one or more backing layers and at least one layer of adhesive on the same side of the adhesive construction as the first adhesive layer, said area extending from an outer peripheral edge of the layered adhesive construction to the edge of the hole and being formed without said moldable paste layer for better attachment thereof to the perianal area.

2. The layered adhesive construction according to claim 1 wherein the hole divides the central axis of symmetry in two parts; a short part and a long part.

3. The layered adhesive construction according to claim 2 wherein the adhesive construction includes (i) an area around the short part of the central axis of symmetry, or (ii) an area around the short part and the long part of the central axis of symmetry, where the area of the layered adhesive construction without the moldable paste layer has one or more backing layers and at least one layer of adhesive on the same side of the adhesive construction as the first adhesive layer.

4. The layered adhesive construction according to claim 1 wherein said area(s) around said part(s) of the central axis of symmetry include one or more backing layers and a layer of the same adhesive as in the first adhesive layer.

5. The layered adhesive construction according to claim 1 wherein said area(s) around said part(s) of the central axis of symmetry include one or more backing layers and a second layer of an adhesive, which is different from the adhesive in the first adhesive layer.

6. The layered adhesive construction according to claim 1 wherein said area(s) around said part(s) of the central axis of symmetry include one or more backing layers and two layers of adhesives on top of each other, where an adhesive layer corresponding to the first adhesive layer is situated between said one or more backing layers and a second adhesive layer.

7. The layered adhesive construction according to claim 1 wherein the layer of moldable paste is wrapped between wrapping layers, which are identical.

8. The layered adhesive construction according to claim 1 wherein the layer of moldable paste is wrapped between wrapping layers, which are different in chemical composition, physical structure and/or thickness.

9. The layered adhesive construction according to claim 7 wherein the wrapping layer(s) is selected from moldable backing layers.

10. The layered adhesive construction according to claim 1 wherein the backing layer(s) carrying the adhesive layer in said area(s) around said part(s) of the central axis of symmetry is identical to one or more of the wrapping layers.

11. The layered adhesive construction according to claim 1 wherein the backing layer(s) carrying the adhesive layer in said area(s) around said part(s) of the central axis of symmetry is different from the wrapping layers.

12. The layered adhesive construction according to claim 1 wherein the thickness of the first adhesive layer is less than one half of the thickness of the layer of the moldable paste where the layers are thickest.

13. The layered adhesive construction according to claim 12 wherein the thickness of the first adhesive layer is one third or less than one third of the thickness of the layer of the moldable paste where the layers are thickest.

14. The layered adhesive construction according to claim 1 wherein the thickness of the layer of the moldable paste is between 1-2.5 mm.

15. The layered adhesive construction according to claim 14 wherein the thickness of the first adhesive layer is 0.5 mm and the thickness of the layer of the moldable paste is 1.5 mm.

16. The layered adhesive construction according to claim 1 wherein both the first adhesive layer and the layer of the moldable paste have a uniform thickness.

17. The layered adhesive construction according to claim 1 wherein the thickness of the adhesive layer in said area(s) around said part(s) of the central axis of symmetry corresponds to the total thickness of the first adhesive layer and the layer of moldable paste.

18. The layered adhesive construction according to claim 1, further comprising a collecting bag or collecting device attached to the wrapping layer of the layered adhesive construction on the surface opposite the first adhesive layer to form a collecting device.

19. A layered adhesive construction for attachment to skin of the perianal area of a patient comprising:
a layered adhesive body having a hole therethrough;
a first region of said body surrounding a first edge portion of said hole and including a layer of a moldable paste wrapped in at least one wrapping layer, and a first adhesive layer attached to the wrapping layer on one outer surface of said layer of wrapped moldable paste; and
a second region of said body in which said layer of moldable paste and said first adhesive layer is replaced by one or more backing layers and at least one layer of adhesive on the same side of the adhesive construction as the first adhesive layer, said second region surrounding a remaining edge portion of said hole and extending from said remaining edge portion to an outer peripheral edge of said layered construction and being configured for adhesive attachment to the perianal skin of the patient.

* * * * *